United States Patent
Ding et al.

(10) Patent No.: US 11,440,793 B2
(45) Date of Patent: Sep. 13, 2022

(54) HYDROGEN SENSOR ON MEDIUM OR LOW TEMPERATURE SOLID MICRO HEATING PLATFORM

(71) Applicant: Shanghai Jiaotong University, Shanghai (CN)

(72) Inventors: Guifu Ding, Shanghai (CN); Qi Liu, Shanghai (CN); Yan Wang, Shanghai (CN); Yunna Sun, Shanghai (CN)

(73) Assignee: Shanghai Jiaotong University, Shanghai (CN)

( * ) Notice: Subject to any disclaimer, the term of this patent is extended or adjusted under 35 U.S.C. 154(b) by 428 days.

(21) Appl. No.: 16/726,272

(22) Filed: Dec. 24, 2019

(65) Prior Publication Data

US 2020/0239300 A1 Jul. 30, 2020

(30) Foreign Application Priority Data

Jan. 25, 2019 (CN) .......................... 201910073967.5

(51) Int. Cl.
*B81B 7/00* (2006.01)
*G01N 33/00* (2006.01)

(52) U.S. Cl.
CPC .......... *B81B 7/0087* (2013.01); *B81B 7/0019* (2013.01); *G01N 33/005* (2013.01); *B81B 2201/0214* (2013.01)

(58) Field of Classification Search
CPC .............. B81B 7/0087; B81B 7/0019; B81B 2201/0214; B81B 7/0096; G01N 33/005
See application file for complete search history.

(56) References Cited

U.S. PATENT DOCUMENTS

| 2008/0054382 A1* | 3/2008 | Stetter | B81B 3/0059 257/E27.001 |
| 2013/0209315 A1* | 8/2013 | Kimura | G01N 25/4826 422/88 |
| 2017/0276626 A1* | 9/2017 | Wei | G01N 33/0062 |

FOREIGN PATENT DOCUMENTS

WO    WO-2005088285 A1 *  9/2005   ............. G01N 27/16

OTHER PUBLICATIONS

Materials Properties Table, Jun. 2002 (Year: 2022).*

* cited by examiner

*Primary Examiner* — Yasser A Abdelaziez
(74) *Attorney, Agent, or Firm* — JCIP Global Inc.

(57) ABSTRACT

Described herein is a hydrogen sensor on medium or low temperature solid micro heating platform, comprising: a substrate; a thermal-insulating layer disposed above the substrate; a heating structure disposed above the thermal-insulating layer, and thermally and electrically isolated from the substrate by the thermal-insulating layer; a thermal-conducting layer covering the heating structure; and a sensitive layer disposed on the thermal-conducting layer. The sensitive layer can be heated to a set temperature by the heating structure to improve sensitivity and reduce the response time.

11 Claims, 6 Drawing Sheets

HYDROGEN SENSOR ON MEDIUM OR LOW TEMPERATURE SOLID MICRO HEATING PLATFORM

CROSS-REFERENCE TO RELATED APPLICATION

This application claims the priority benefit of China application serial no. 201910073967.5, filed on Jan. 25, 2019. The entirety of the above-mentioned patent application is hereby incorporated by reference herein and made a part of this specification.

TECHNICAL FIELD

This invention relates generally to the technical field of micro machining and micro-electro-mechanical system (MEMS). More particularly, the invention relates to an ultra-low power consumption medium or low temperature solid micro heating platform and a high-performance hydrogen sensor on the micro heating platform.

BACKGROUND

With the increasing demand for miniaturization and low power consumption of sensors, more and more attention has been paid to the micro heating platform gas sensors which integrate sensitive materials with the micro heating platform. The most commonly used gas sensitive materials are some semiconductor metal oxides. The working temperature of these sensors is as high as 200° C. to 450° C., so the micro heating platform structures are usually required to achieve thermal isolation and reduce power consumption.

The existing micro heating platform structure includes continuous film and suspended film, which are formed by backside etching and frontside etching respectively. Among them, the suspended film has been widely studied because it can significantly reduce power consumption. But the process for the suspended micro heating platform is complicated, the yield is not high, the structural strength and stability are poor. The insulation layer of the current micro heating platform usually uses inorganic insulating materials such as silicon oxide and silicon nitride, but the cost for depositing silicon oxide and silicon nitride is higher, and process cycle is long.

In view of the problems of complicated fabrication process, high cost, low structural strength and poor stability existing in the existing micro heating platform structure, the present application proposes a new medium or low temperature solid micro heating platform with ultra-low power consumption which at least in part overcomes some of the problems. Moreover, the palladium or palladium alloy thin film hydrogen sensor based on the solid micro heating platform may achieve high sensitivity and fast response and so on.

BRIEF SUMMARY

In view of the problems existing in the current micro heating platform, such as complicated fabrication process, high cost, low structural strength and poor stability, according to one aspect of present application, it provides a hydrogen sensor on medium or low temperature solid micro heating, comprising: a substrate; a thermal-insulating layer disposed above the substrate; a heating structure disposed above the thermal-insulating layer, and isolated, thermally and electrically, from the substrate by the thermal-insulating layer; a thermal-conducting layer covering the heating structure; and a sensitive layer disposed on the thermal-conducting layer, wherein the sensitive layer is heated to a set temperature by the heating structure to improve sensitivity and reduce the response time.

In one embodiment, the material of the substrate may be glass, ceramics, or organic substrate.

In one embodiment, the thermal-insulating layer may be disposed on the bottom and sides of the heating structure.

In one embodiment, the material of the thermal-insulating layer may be an insulating material having a thermal conductivity of less than 0.12 W/(m*K). The material of the thermal-insulating layer may be organic colloid doped with inorganic nanoparticles or whiskers of low thermal conductivity. The material of the thermal-insulating layer may be polyimide doped with 2 wt %-10 wt % nano silicon dioxide with a thickness of 30 microns to 100 microns.

In one embodiment, the heating structure may be a heating wire or a heating film.

In one embodiment, the heating structure may be a platinum (Pt) heating wire with a line width of 5 microns to 10 microns, and a thickness of 100 nanometers to 300 nanometers.

In one embodiment, the material of the thermal-conducting layer may be an insulating material having a thermal conductivity of more than 1.5 W/(m*K). The material of the thermal-conducting layer may be organic colloid doped with inorganic nanoparticles or whiskers of high thermal conductivity. The material of the thermal-conducting layer may be polyimide doped with 2 wt %-10 wt % nano silicon carbide whiskers with a thickness of 4 microns to 10 microns.

In one embodiment, the thermal-conducting layer may have a patterned structure to reduce the area of the thermal-conducting layer covering the heating structure, thereby reducing the heat dissipation.

In one embodiment, the material of the sensitive layer may be a hydrogen-sensitive material including palladium (Pd) or palladium-based alloy with a thickness of 50 nanometers to 200 nanometers.

In one embodiment, the operating temperature of the hydrogen sensor may be no more than 350° C.

The present application provides a medium or low temperature solid micro heating platform with ultra-low power consumption and high performance hydrogen sensor based on the micro heating platform. The solid micro heating platform may be fabricated by forming in turn a thermal-insulating layer, a heating structure and a thermal-conducting layer on the substrate. And then a sensitive layer is formed on the upper surface. The hydrogen sensor based on medium or low temperature solid micro heating platform may have the advantages such as low power consumption and high yield and so on.

BRIEF DESCRIPTION OF THE DRAWINGS

It is to be understood that both the foregoing brief summary and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

In the following description, for the purposes of explanation, numerous specific details are set forth in order to provide a thorough understanding of the embodiments of the invention described below. It will be apparent, however, to one skilled in the art that the embodiments of the invention may be practiced without some of these specific details. In other instances, well-known structures and devices are shown in block diagram form to avoid obscuring the underlying principles of the embodiments of the invention.

In the specification, the reference to "one embodiment" or "the embodiment" means that the specific features, structures or characters described in combination with the embodiment are included in at least one embodiment of the invention. The phrase "in one embodiment" appearing throughout the specification does not necessarily all refer to the same embodiment.

The present application provides a medium or low temperature solid micro heating platform with ultra-low power consumption and high performance hydrogen sensor based on the micro heating platform. The solid micro heating platform may be fabricated by forming in turn a thermal-insulating layer, a heating structure and a thermal-conducting layer on the substrate. And then a sensitive layer is formed on the upper surface. The hydrogen sensor based on the medium or low temperature solid micro heating platform may have the advantages such as low power consumption and high yield and so on.

Figure 1:
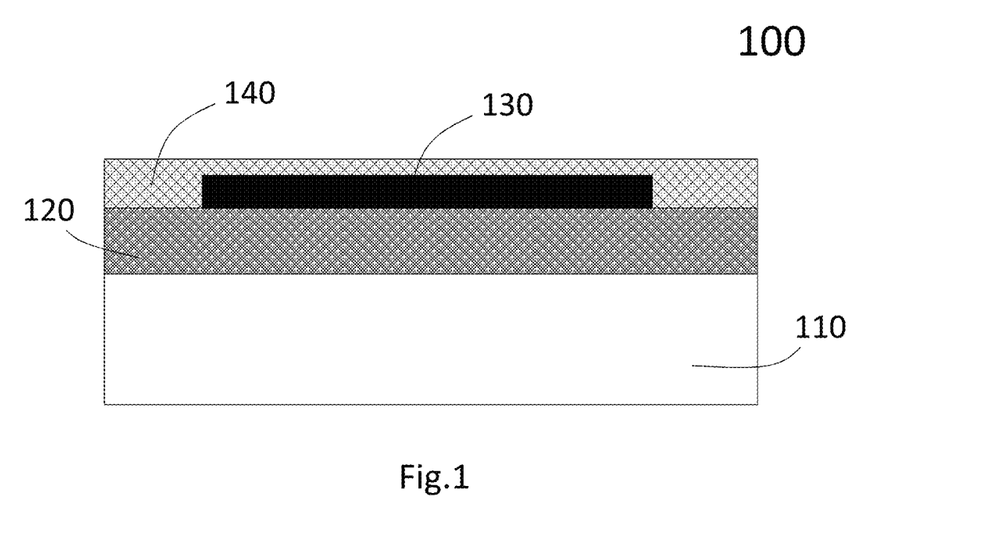
FIG. 1 shows the section diagram of the medium or low temperature solid micro heating platform 100 with ultra-low power consumption according to one embodiment of present application.

The medium or low temperature solid micro heating platform with ultra-low power consumption according to one embodiment of present application is described in detail in connection with FIG. 1. FIG. 1 shows the section diagram of the medium or low temperature solid micro heating platform 100 with ultra-low power consumption according to one embodiment of present application. As shown in FIG. 1, the medium or low temperature solid micro heating platform with ultra-low power consumption may comprise a substrate 110, a thermal-insulating layer 120, a heating structure 130, and a thermal-conducting layer 140.

The substrate 110 is used to support the micro heating platform. The material of the substrate 110 may be an inorganic material such as glass, ceramics, etc., or organic substrate material. In one embodiment of the invention, the substrate 110 may be a glass substrate with a thickness of 1 mm.

The thermal-insulating layer 120 is disposed above the substrate 110, and is a poor conductor of heat, for preventing heat conduction. At the same time, the thermal-insulating layer 120 is an insulator. The material of the thermal-insulating layer 120 may be an insulating material having a thermal conductivity of less than 0.12 W/(m*K). The thermal-insulating layer 120 may be formed by doping organic colloid (such as polyimide and benzocyclobutene) with low thermal conductivity inorganic nanoparticles or whiskers (such as nano silicon dioxide, potassium hexatitanate whiskers, etc.). In one embodiment of the present invention, the thermal-insulating layer 120 may be formed by doping polyimide with silicon dioxide. The material of the thermal-insulating layer is polyimide doped with 2 wt %-10 wt % nano silicon dioxide with a thickness of 30 microns to 100 microns. In a specific embodiment of the present invention, the material of the thermal-insulating layer 120 is polyimide doped with about 5 wt % nano silicon dioxide with a thickness of about 50 microns.

The heating structure 130 is a heating device for the micro heating platform, and is disposed above the thermal-insulating layer 120. The heating structure 130 is isolated thermally and electrically from the substrate 110 by the thermal-insulating layer 120. The heating structure 130 may be a heating structure such as a heating wire or a heating film. In some embodiments of the present invention, the heating structure 130 is a platinum (Pt) heating wire with a line width of 5 microns to 10 microns, and a thickness of 100 nanometers to 300 nanometers. In one particular embodiment of the present invention, the heating structure 130 is composed of a platinum (Pt) heating wire with a shape of double spiral, an area of 200×200 square microns, a line width of 10 microns, and a thickness of 200 nanometers.

The thermal-conducting layer 140 is disposed above the thermal-insulating layer 120 and cover the heating structure 130. The thermal-conducting layer 140 is a good conductor of heat, for transferring the heat generated by the heating structure 130 to the surface and facilitating lateral heat transfer to improve the temperature uniformity of the micro heating platform. Meanwhile, the thermal-conducting layer 140 is an insulator. The material of the thermal-conducting layer 140 may be an insulating material having a thermal conductivity of more than 1.5 W/(m*K). Thus, the thermal-conducting layer may be organic colloid doped with inorganic nanoparticles or whiskers of a high thermal conductivity, such as nano silicon carbide whisker and nano aluminum nitride particles. In one embodiment of the present invention, the thermal-conducting layer 140 may be formed by doping polyimide with the silicon carbide. The material of the thermal-conducting layer is polyimide doped with 2 wt %-10 wt % nano silicon carbide whiskers with a thickness of 4 microns to 10 microns. In one particular embodiment of the present invention, the material of thermal-conducting layer 140 is polyimide doped with about 5 wt % nano silicon carbide whiskers with a thickness of about 6 microns.

FIGS. 2A-2D show the section diagrams of a process for forming the medium or low temperature solid micro heating platform 100 with ultra-low power consumption according to one embodiment of present application. The process for forming the medium or low temperature solid micro heating platform 100 with ultra-low power consumption is described in connection with FIGS. 2A-2D.

Figure 2A:
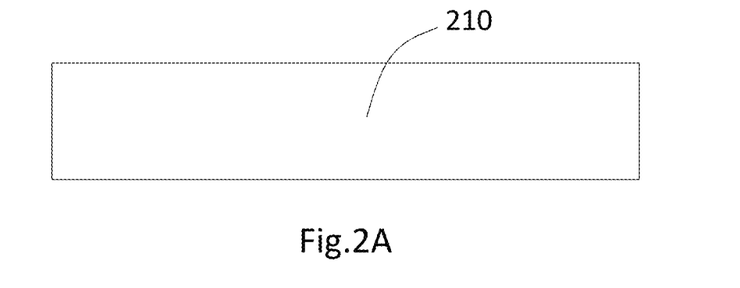
FIGS. 2A-2D show the section diagrams of a process for forming the medium or low temperature solid micro heating platform 100 with ultra-low power consumption according to one embodiment of present application.

At first, as shown in FIG. 2A, the substrate 210 is provided. The substrate 210 is used to support the micro heating platform. The material of the substrate 210 may be an inorganic material such as glass, ceramics, etc., or organic substrate material. In one embodiment of the invention, the substrate 210 may be a glass substrate with a thickness of 1 mm.

Figure 2B:
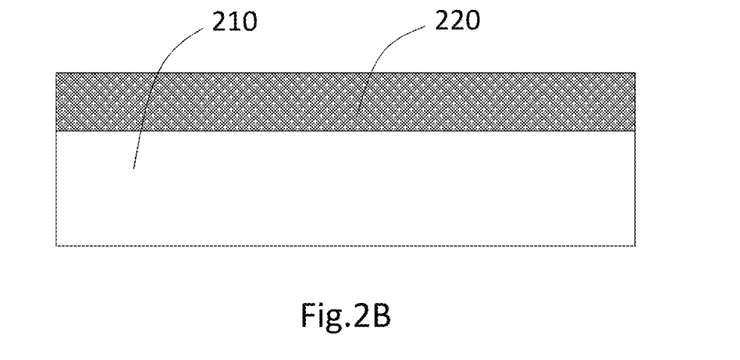

Next, as shown in FIG. 2B, the thermal-insulating layer 220 is formed on the substrate 210. The thermal-insulating layer 220 may be disposed on the substrate 210 by means of spin coating, deposition, and the like. The thermal-insulating layer 220 is a poor conductor of heat, for preventing heat conduction. At the same time, the thermal-insulating layer 220 is an insulator. In one embodiment of the present invention, the thermal-insulating layer 220 may be formed by doping polyimide with silicon dioxide. In a specific embodiment of the present invention, the material of the thermal-insulating layer 220 is polyimide doped with about 5 wt % nano silicon dioxide, with a thickness of about 50 microns.

Figure 2C:
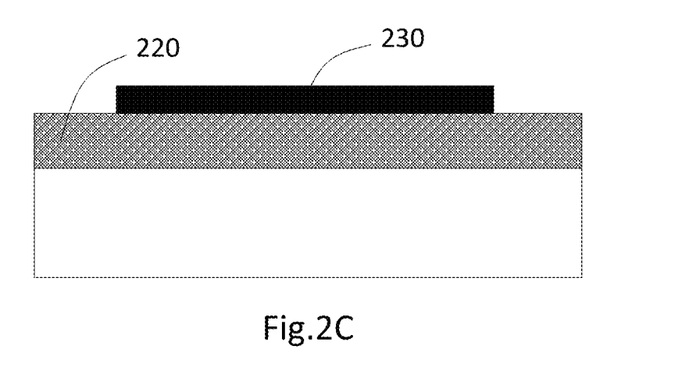

Then, as shown in FIG. 2C, the heating structure 230 is formed on the thermal-insulating layer 220. The heating structure 230 is a heating device for the micro heating platform. The heating structure 230 is isolated thermally and electrically from the substrate 210 by the thermal-insulating layer 220. The heating structure 230 may be a heating structure such as a heating wire or a heating film. In one embodiment of the present invention, the heating structure 230 is composed of a platinum (Pt) heating wire with a shape of double spiral, an area of 200×200 square microns, a line width of 10 microns, and a thickness of 200 nanometers.

Figure 2D:
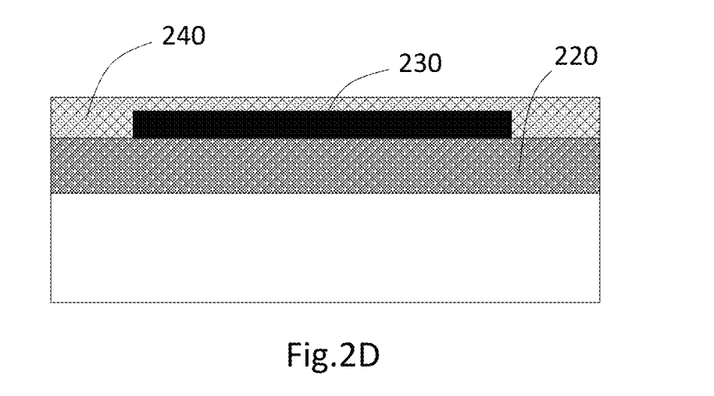

Finally, as shown in FIG. 2D, the thermal-conducting layer 240 is formed to cover the heating structure 230. The thermal-conducting layer 240 is a good conductor of heat, for transferring the heat generated by the heating structure 230 to the surface and facilitating lateral heat transfer to improve the temperature uniformity of the micro heating platform. Meanwhile, the thermal-conducting layer 240 is an insulator. In one embodiment of the present invention, the thermal-conducting layer 240 may be formed by doping polyimide with the silicon carbide. In one particular embodiment of the present invention, the material of thermal-conducting layer 240 is polyimide doped with about 5 wt % nano silicon carbide whiskers with a thickness of about 6 microns.

Figure 3:
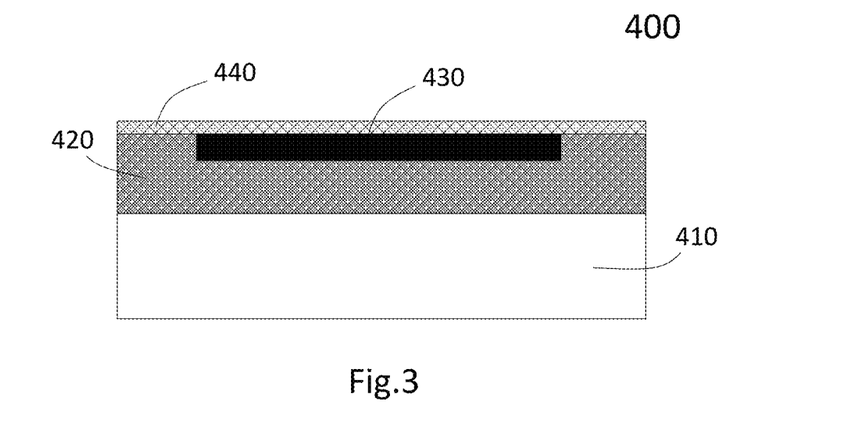
FIG. 3 shows the section diagram of the medium or low temperature solid micro heating platform 400 with ultra-low power consumption according to another embodiment of present application.

FIG. 3 shows the section diagram of the medium or low temperature solid micro heating platform 400 with ultra-low power consumption according to another embodiment of present application. As shown in FIG. 3, the medium or low temperature solid micro heating platform 400 with ultra-low power consumption may comprise a substrate 410, a thermal-insulating layer 420, a heating structure 430, and a thermal-conducting layer 440. The difference from the embodiment shown in FIG. 1 is that the thermal-insulating layer 420 of the medium or low temperature solid micro heating platform 400 with ultra-low power consumption is also provided on the side of the heating structure 430 in addition to providing between the substrate 410 and the heating structure 430, so that a better thermal isolation to the heating structure 430 may be achieved. This structure may also be described as the heating structure 430 embedded into the thermal-insulating layer 420. It may be formed by forming grooves in the thermal-insulating layer 420 and then forming the heating structure 430 by pattern plating or damascene process. Compared with the medium or low temperature solid micro heating platform 100, the medium or low temperature solid micro heating platform 400 may have better thermal insulation effect, faster heating capacity, and lower power consumption.

Figure 4:
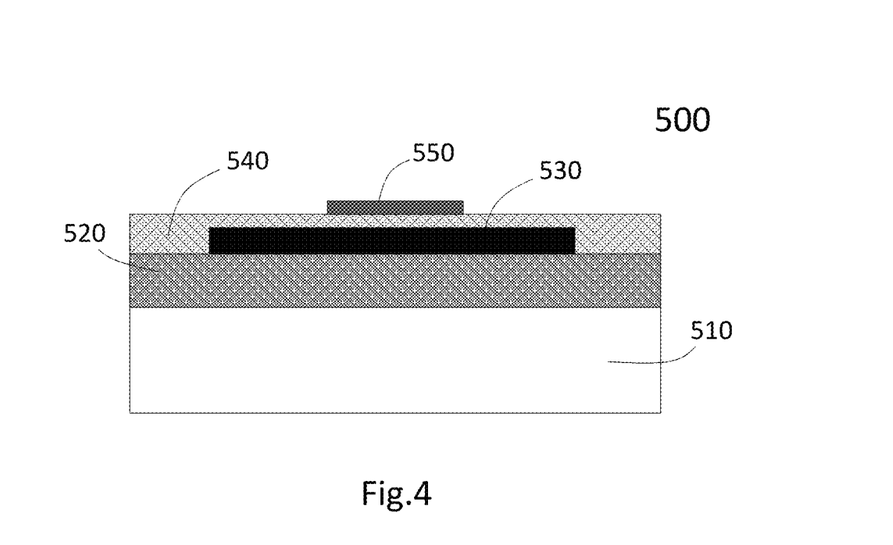
FIG. 4 shows the section diagram of the sensor 500 based on the medium or low temperature solid micro heating platform with ultra-low power consumption according to one embodiment of present application.
Figure 5A:
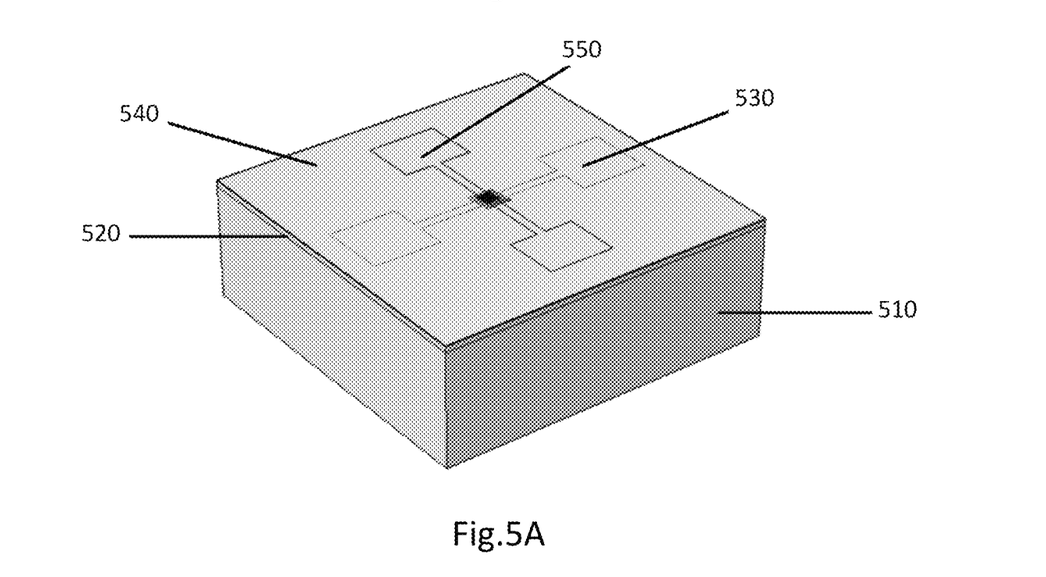
FIGS. 5A and 5B show the stereograms of the sensor 500 based on the medium or low temperature solid micro heating platform with ultra-low power consumption according to one embodiment of present application.
Figure 5B:
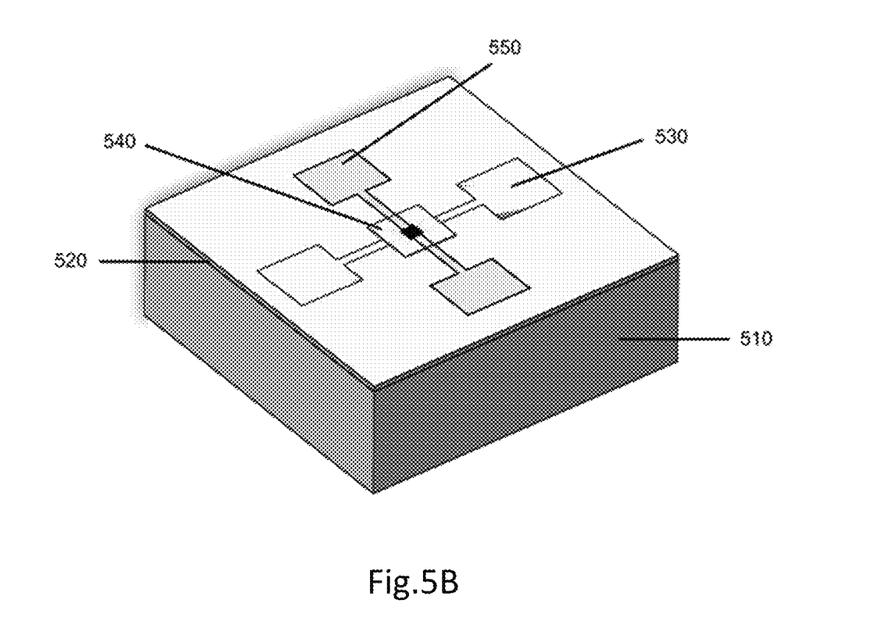

The hydrogen sensor based on the medium or low temperature solid micro heating platform with ultra-low power consumption according to one embodiment of present application is described in detail in connection with FIGS. 4, 5A, and 5B. FIG. 4 shows the section diagram of the hydrogen sensor 500 based on the medium or low temperature solid micro heating platform with ultra-low power consumption according to one embodiment of present application. FIGS. 5A and 5B show the stereograms of the hydrogen sensor 500 based on the medium or low temperature solid micro heating platform with ultra-low power consumption according to one embodiment of present application. As shown in FIGS. 4, 5A, and 5B, the hydrogen sensor 500 based on the medium or low temperature solid micro heating platform with ultra-low power consumption may comprise a substrate 510, a thermal-insulating layer 520, a heating structure 530, a thermal-conducting layer 540, and a sensitive layer 550. The thermal-conducting layer in FIG. 5A may cover the whole surface, while the thermal-conducting layer in FIG. 5B may only cover the heating area by patterning, with an area of 400×400 square microns.

The substrate 510, the thermal-insulating layer 520, the heating structure 530, and the thermal-conducting layer 540 are similar to the same in previous embodiment, and will not be described here. The sensitive layer 550 is provided above the thermal-conducting layer 540, so that it can be heated to a set temperature by the heating structure 530. The high performance, such as high sensitivity and fast response, may be achieved by increasing the temperature of the sensitive layer through the solid micro heating platform. In one embodiment of present invention, the sensor 500 is a gas-sensitive sensor for detecting hydrogen, and the sensitive layer 550 is a hydrogen-sensitive material, using palladium (Pd) sensitive film and a palladium test electrode, with a shape of double spiral, an area of 150×150 square microns, a line width of 10 microns, and a thickness of about 150 nanometers. The maximum operating temperature of the hydrogen sensor 500 based on the medium or low temperature solid micro heating platform with ultra-low power consumption does not exceed 350° C., and the long-term continuous operating temperature does not exceed 300° C.

FIGS. 6A-6F show the section diagrams of a process for forming the sensor 500 based on the medium or low temperature solid micro heating platform with ultra-low power consumption according to one embodiment of present application.

Figure 6A:
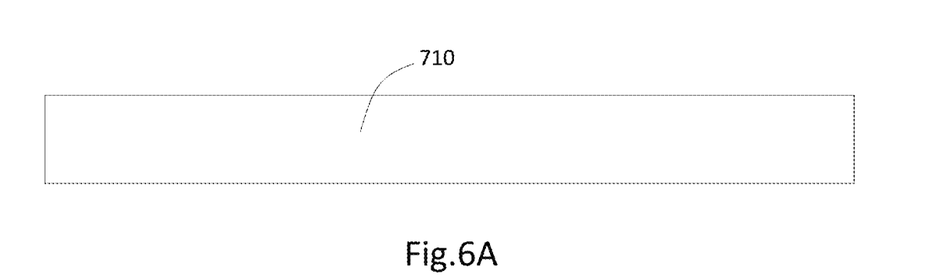
FIGS. 6A-6F show the section diagrams of a process for forming the sensor 500 based on the medium or low temperature solid micro heating platform with ultra-low power consumption according to one embodiment of present application.

At first, as shown in FIG. 6A, the substrate 710 is provided. The substrate 710 is used to support the micro heating platform. The material of the substrate 710 may be an inorganic material such as glass, ceramics, etc., or organic substrate material. In one embodiment of the invention, the substrate 710 may be a glass substrate with a thickness of 1 mm.

Figure 6B:
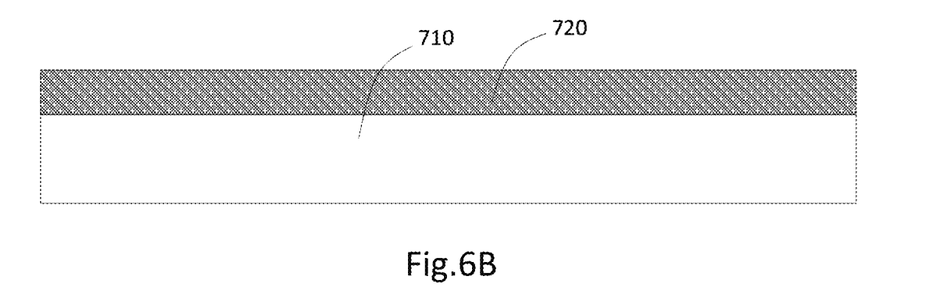

Next, as shown in FIG. 6B, the thermal-insulating layer 720 is formed on the substrate 710. The thermal-insulating layer 720 may be disposed on the substrate 710 by means of spin coating, deposition, and the like. The thermal-insulating layer 720 is a poor conductor of heat, for preventing heat conduction. At the same time, the thermal-insulating layer 720 is an insulator. In one embodiment of the present invention, the thermal-insulating layer 720 may be formed by doping polyimide with silicon dioxide. In a specific embodiment of the present invention, the material of the thermal-insulating layer 720 is polyimide doped with about 5 wt % nano silicon dioxide, with a thickness of about 50 microns.

Figure 6C:
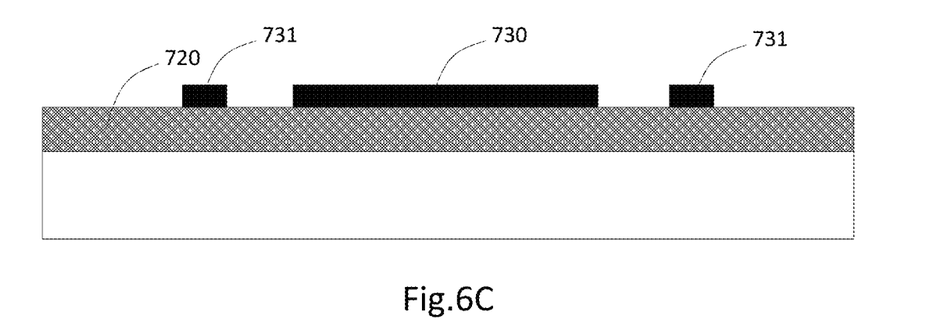

Then, as shown in FIG. 6C, the heating structure 730 and electrode pair 731 are formed on the thermal-insulating layer 720. The heating structure 730 and electrode pair 731 may be formed by patterned plating or deposition process. The heating structure 730 is a heating device for the micro heating platform. The heating structure 730 is isolated thermally and electrically from the substrate 710 by the thermal-insulating layer 720, thus preventing the heat generated from being easily transferred to the substrate 710. The heating structure 730 may be heating wire, a heating film, or the like. In one embodiment of the present invention, the heating structure 730 is composed of a platinum (Pt) heating wire and platinum electrode pair 731 with a shape of double spiral, an area of 200×200 square microns, a line width of 10 microns, and a thickness of 200 nanometers.

Figure 6D:
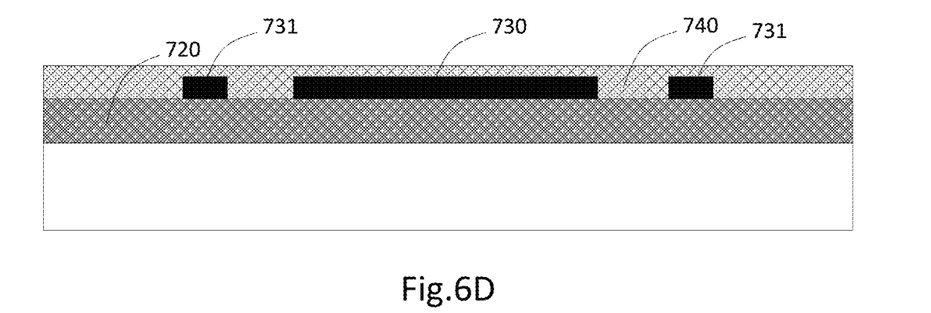

Next, as shown in FIG. 6D, the thermal-conducting layer 740 is formed to cover the heating structure 730. The thermal-conducting layer 740 may be formed by means of spin coating, deposition, and the like. The thermal-conducting layer 740 is a good conductor of heat, for transferring the heat generated by the heating structure 730 to the surface and facilitating lateral heat transfer to improve the temperature uniformity of the micro heating platform. Meanwhile, the thermal-conducting layer 740 is an insulator. In one embodiment of the present invention, the thermal-conducting layer 740 may be formed by doping polyimide with silicon carbide. In one particular embodiment of the present invention, the material of thermal-conducting layer 740 is polyimide doped with about 5 wt % nano silicon carbide whiskers, with a thickness of about 6 microns.

Figure 6E:
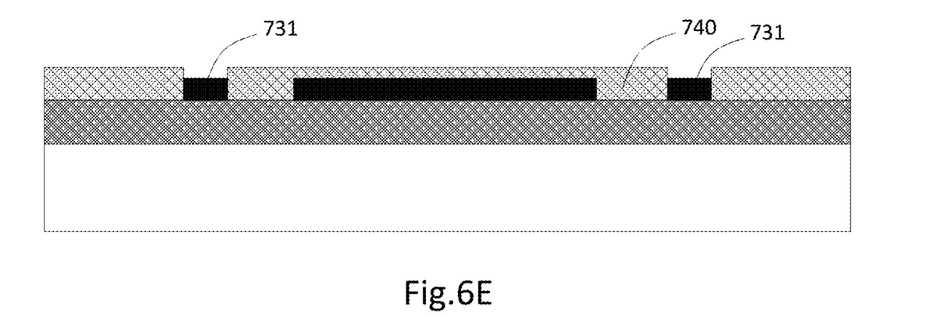

Then, as shown in FIG. 6E, the electrode pair 731 of the heating structure 730 is exposed. The specific exposing process can be realized by patterned etching.

Figure 6F:
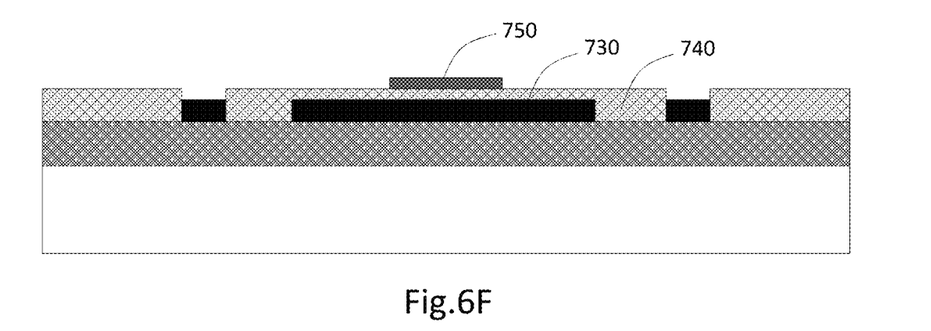

Finally, as shown in FIG. 6F, the sensitive layer 750 is provided above the thermal-conducting layer 740 covering the heating structure 730, so that it can be heated to a set temperature by the heating structure 730. The high performance, such as high sensitivity and fast response, may be achieved by increasing the temperature of the sensitive layer through the solid micro heating platform. In one embodiment of present invention, the sensor is a gas-sensitive sensor for detecting hydrogen, and the sensitive layer 750 is a hydrogen-sensitive material, using palladium (Pd) sensitive film and a palladium test electrode, with a shape of double spiral, an area of 150×150 square microns, a line width of 10 microns, and a thickness of about 150 nanometers. The maximum operating temperature of the hydrogen sensor 500 based on the medium or low temperature solid micro heating platform with ultra-low power consumption does not exceed 350° C., and the long-term continuous operating temperature does not exceed 300° C.

Figure 7:
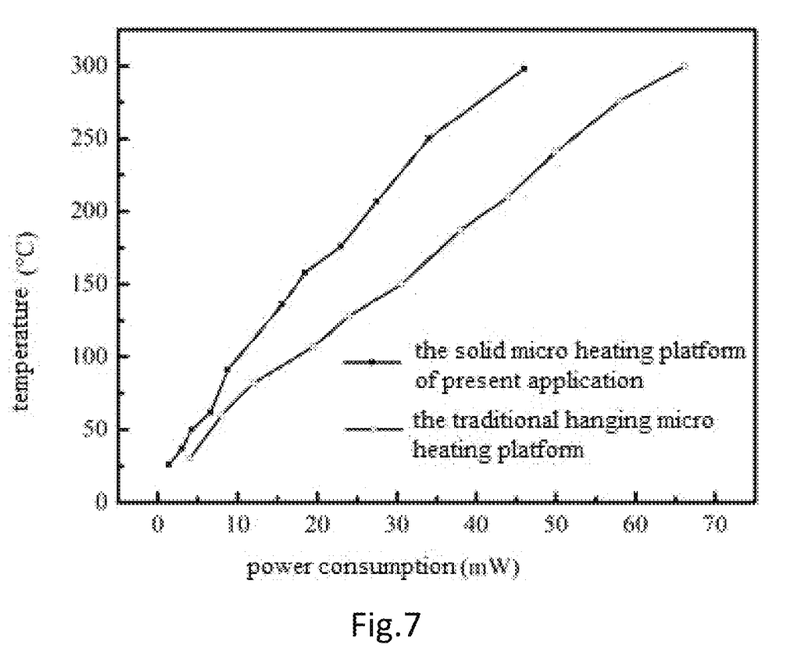
FIG. 7 shows a comparison diagram between the curve of power consumption versus temperature of the hydrogen sensor on the medium or low temperature solid micro heating platform with ultra-low power consumption according to one embodiment of present application and the curve of power consumption versus temperature of the hydrogen sensor on the traditional hanging micro heating platform with the same heating area.

FIG. 7 shows a comparison diagram between the curve of power consumption versus temperature of the hydrogen sensor on the medium or low temperature solid micro heating platform with ultra-low power consumption according to one embodiment of present application and the curve of power consumption versus temperature of the hydrogen sensor of the hanging micro heating platform with the same heating area. It can be seen from FIG. 7 that the hydrogen sensor on the medium or low temperature solid micro heating platform of present application may have a lower power consumption and a faster heating curve.

Figure 8:
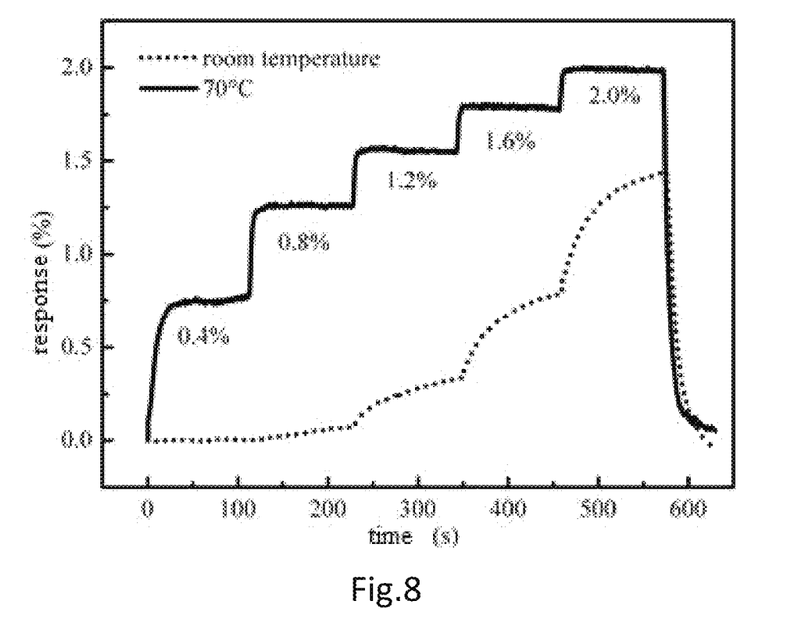
FIG. 8 shows a comparison graph of response curves of the hydrogen sensor on the medium or low temperature solid micro heating platform with ultra-low power consumption according to one embodiment of present application at room temperature and in heating state.

FIG. 8 shows a comparison graph of response curves of the hydrogen sensor on the medium or low temperature solid micro heating platform with ultra-low power consumption according to one embodiment of present application at room temperature and in heating state. Therefore, the sensor has more sensitive and faster detection performance when raising the temperature of the micro heating platform.

The present application provides a medium or low temperature solid micro heating platform with ultra-low power consumption and high performance hydrogen sensor based on the micro heating platform. The solid micro heating platform may be fabricated by forming in turn a thermal-insulating layer, a heating structure and a thermal-conducting layer on the substrate. And then a sensitive layer is formed on the upper surface. The hydrogen sensor based on medium or low temperature solid micro heating platform may have the advantages such as low power consumption and high yield and so on.

While the embodiments disclosed herein have been set forth for the purpose of illustration, the foregoing description should not be deemed to be a limitation on the scope of the disclosure or the appended claims. Accordingly, various modifications, adaptations, and alternatives may occur to one skilled in the art without departing from the spirit and scope of the present disclosure or the appended claims.

What is claimed is:

1. A hydrogen sensor on medium or low temperature solid micro heating platform, comprising:
   a substrate;
   a thermal-insulating layer disposed above the substrate;
   a heating structure disposed above the thermal-insulating layer, and isolated, thermally and electrically, from the substrate by the thermal-insulating layer;
   a thermal-conducting layer covering the heating structure, wherein the thermal-conducting layer has a patterned structure to reduce the area of the thermal-conducting layer covering the heating structure, thereby reducing the heat dissipation; and
   a sensitive layer disposed on the thermal-conducting layer, wherein the sensitive layer is heated to a set temperature by the heating structure to improve sensitivity and reduce the response time, wherein the material of the sensitive layer is a hydrogen-sensitive material including palladium (Pd) or palladium-based alloy.

2. The hydrogen sensor on medium or low temperature solid micro heating platform of claim 1, wherein the material of the substrate is glass, ceramics, or organic substrate.

3. The hydrogen sensor on medium or low temperature solid micro heating platform of claim 1, wherein the thermal-insulating layer is disposed on the bottom and sides of the heating structure.

4. The hydrogen sensor on medium or low temperature solid micro heating platform of claim 1, wherein the material of the thermal-insulating layer is an insulating material having a thermal conductivity of less than 0.12 W/(m*K);
  wherein the material of the thermal-insulating layer is organic colloid doped with inorganic nanoparticles or whiskers of low thermal conductivity; or
  wherein the material of the thermal-insulating layer is polyimide doped with 2 wt %-10 wt % nano silicon dioxide with a thickness of 30 microns to 100 microns.

5. The hydrogen sensor on medium or low temperature solid micro heating platform of claim 1, wherein the heating structure is a heating wire or a heating film.

6. The hydrogen sensor on medium or low temperature solid micro heating platform of claim 5, wherein the heating structure is a platinum (Pt) heating wire with a line width of 5 microns to 10 microns, and a thickness of 100 nanometers to 300 nanometers.

7. The hydrogen sensor on medium or low temperature solid micro heating platform of claim 1, wherein the material of the thermal-conducting layer is an insulating material having a thermal conductivity of more than 1.5 W/(m*K);
  wherein the material of the thermal-conducting layer is organic colloid doped with inorganic nanoparticles or whiskers of high thermal conductivity; or
  wherein the material of the thermal-conducting layer is polyimide doped with 2 wt %-10 wt % nano silicon carbide whiskers with a thickness of 4 microns to 10 microns.

8. The hydrogen sensor on medium or low temperature solid micro heating platform of claim 1, wherein thickness of the sensitive layer is from 50 nanometers to 200 nanometers.

9. The hydrogen sensor on medium or low temperature solid micro heating platform of claim 1, wherein the operating temperature of the hydrogen sensor is no more than 350° C.

10. A hydrogen sensor on medium or low temperature solid micro heating platform, comprising:
  a substrate;
  a thermal-insulating layer disposed above the substrate, wherein the material of the thermal-insulating layer is an insulating material having a thermal conductivity of less than 0.12 W/(m*K);
  wherein the material of the thermal-insulating layer is organic colloid doped with inorganic nanoparticles or whiskers of low thermal conductivity; or
  wherein the material of the thermal-insulating layer is polyimide doped with 2 wt %-10 wt % nano silicon dioxide with a thickness of 30 microns to 100 microns;
  a heating structure disposed above the thermal-insulating layer, and isolated, thermally and electrically, from the substrate by the thermal-insulating layer;
  a thermal-conducting layer covering the heating structure; and
  a sensitive layer disposed on the thermal-conducting layer, wherein the sensitive layer is heated to a set temperature by the heating structure to improve sensitivity and reduce the response time, wherein the material of the sensitive layer is a hydrogen-sensitive material including palladium (Pd) or palladium-based alloy.

11. A hydrogen sensor on medium or low temperature solid micro heating platform, comprising:
  a substrate;
  a thermal-insulating layer disposed above the substrate;
  a heating structure disposed above the thermal-insulating layer, and isolated, thermally and electrically, from the substrate by the thermal-insulating layer;
  a thermal-conducting layer covering the heating structure, wherein the material of the thermal-conducting layer is an insulating material having a thermal conductivity of more than 1.5 W/(m*K);
  wherein the material of the thermal-conducting layer is organic colloid doped with inorganic nanoparticles or whiskers of high thermal conductivity; or
  wherein the material of the thermal-conducting layer is polyimide doped with 2 wt %-10 wt % nano silicon carbide whiskers with a thickness of 4 microns to 10 microns; and
  a sensitive layer disposed on the thermal-conducting layer, wherein the sensitive layer is heated to a set temperature by the heating structure to improve sensitivity and reduce the response time, wherein the material of the sensitive layer is a hydrogen-sensitive material including palladium (Pd) or palladium-based alloy.

* * * * *